(12) United States Patent
Sato et al.

(10) Patent No.: US 11,363,844 B2
(45) Date of Patent: Jun. 21, 2022

(54) MASK

(71) Applicant: NBC MESHTEC INC., Tokyo (JP)

(72) Inventors: Tetsuya Sato, Shizuoka (JP);
Tomokazu Nagao, Tokyo (JP); Tsuruo Nakayama, Tokyo (JP)

(73) Assignee: NBC MESHTEC INC., Tokyo (JP)

( * ) Notice: Subject to any disclaimer, the term of this patent is extended or adjusted under 35 U.S.C. 154(b) by 399 days.

(21) Appl. No.: 16/332,472

(22) PCT Filed: Oct. 13, 2017

(86) PCT No.: PCT/JP2017/037107
§ 371 (c)(1),
(2) Date: Mar. 12, 2019

(87) PCT Pub. No.: WO2018/074337
PCT Pub. Date: Apr. 26, 2018

(65) Prior Publication Data
US 2019/0231004 A1 Aug. 1, 2019

(30) Foreign Application Priority Data

Oct. 17, 2016 (JP) .............................. JP2016-203340

(51) Int. Cl.
| | | |
|---|---|---|
| A41D 13/11 | (2006.01) | |
| A62B 18/02 | (2006.01) | |
| A62B 23/02 | (2006.01) | |
| A61K 33/34 | (2006.01) | |
| A61K 33/38 | (2006.01) | |
| A62B 7/10 | (2006.01) | |

(52) U.S. Cl.
CPC .......... *A41D 13/1161* (2013.01); *A41D 13/11* (2013.01); *A41D 13/1192* (2013.01); *A62B 18/02* (2013.01); *A62B 23/025* (2013.01); *A61K 33/34* (2013.01); *A61K 33/38* (2013.01); *A62B 7/10* (2013.01)

(58) Field of Classification Search
CPC .. A41D 13/11–1192; A62B 23/00–025; A62B 18/00–025; A62B 7/00; A62B 7/10; A61K 33/34; A61K 33/38
See application file for complete search history.

(56) References Cited

U.S. PATENT DOCUMENTS

| | | | | |
|---|---|---|---|---|
| 4,941,467 A | * | 7/1990 | Takata .................. | A61M 16/06 128/203.12 |
| 5,620,785 A | * | 4/1997 | Watt ...................... | A41D 13/11 128/206.12 |
| 5,706,804 A | * | 1/1998 | Baumann ............ | A41D 13/1115 128/206.19 |
| 2009/0084384 A1 | * | 4/2009 | Cheng .................. | A62B 23/025 128/206.19 |
| 2010/0307503 A1 | | 12/2010 | Iwamoto et al. | |
| 2012/0082711 A1 | * | 4/2012 | Goranov ................ | A01N 59/16 424/404 |
| 2012/0160247 A1 | | 6/2012 | Quincy, III et al. | |
| 2012/0192876 A1 | | 8/2012 | Fujimori et al. | |
| 2015/0173436 A1 | | 6/2015 | Tsuei | |
| 2019/0059471 A1 | | 2/2019 | Quincy, III et al. | |

FOREIGN PATENT DOCUMENTS

| | | | | |
|---|---|---|---|---|
| CN | 101227954 | | 7/2008 | |
| CN | 104411369 | | 3/2015 | |
| EP | 2473660 B1 | * | 11/2015 | ............ B32B 5/022 |
| JP | 1-192807 | | 8/1989 | |
| JP | 2005-7072 | | 1/2005 | |
| JP | 2007-159796 | | 6/2007 | |
| JP | 2008-86626 | | 4/2008 | |
| JP | 2011-125494 | | 6/2011 | |
| JP | 2014-503288 | | 2/2014 | |
| JP | 2014-198165 | | 10/2014 | |
| TW | 201402171 | | 1/2014 | |
| TW | 201420150 | | 6/2014 | |
| WO | 02/41717 | | 5/2002 | |
| WO | 2007/010969 | | 1/2007 | |
| WO | 2011/040035 | | 4/2011 | |

(Continued)

OTHER PUBLICATIONS

Deng, H.; Reynolds, CT; Cabrera, NO; Barkoula, NM; Alcock, B; Peijs, T; The water absorption behaviour of all-polypropylene composites and its effect on mechanical properties; 2010; Composites: Part B 41; p. 271 (Year: 2010).*

(Continued)

*Primary Examiner* — Michelle J Lee
(74) *Attorney, Agent, or Firm* — Wenderoth, Lind & Ponack, L.L.P.

(57) ABSTRACT

A mask having an inner surface facing a wearer and an outer surface located opposite to the inner surface has first to fourth filters. The first filter is disposed on the outer surface of the mask and has air permeability and a water absorption capacity of 100% or more and less than 1000%. The second filter is layered on the first filter on the side of the inner surface of the mask and has air permeability and a water absorption capacity of less than 30%. The third filter is layered on the second filter on the side of the inner surface of the mask and is formed of an electret filter having air permeability and a water absorption capacity of less than 50%. The fourth filter is disposed on the inner surface of the mask and has air permeability.

6 Claims, No Drawings

(56) References Cited

FOREIGN PATENT DOCUMENTS

| WO | 2014/003156 | 1/2014 |
| WO | 2014/042171 | 3/2014 |

OTHER PUBLICATIONS

Buch, Vyom; Leary, Josh; Water Retention Capacities of Different Fabrics; 2012; Appalachian State University, p. 4 (Year: 2012).*
International Search Report dated Dec. 12, 2017 in International Application No. PCT/JP2017/037107, with English translation.
International Preliminary Report on Patentability dated May 2, 2019 in International Application No. PCT/JP2017/037107.

* cited by examiner

MASK

TECHNICAL FIELD

The present invention relates to a mask that prevents the penetration of blood, droplets, and the like.

BACKGROUND ART

From 2010 onward, in Japan, many natural disasters such as the Northern Kyushu heavy rain and the Kumamoto earthquakes, including the Great East Japan Earthquake, have occurred, and many evacuees have been forced to live evacuation life. In addition, other than natural disasters, incidents causing many casualties, such as terrorist bomb explosions and building fires overseas, have also occurred. The main problem in such situations is measures against infectious diseases for people engaged in relief activities. For many viral infectious diseases, infection spreads through blood, and therefore in relief, it is recommended to wear protective clothing, a mask, a cap, and the like. But, sometimes, the blood of infectious disease patients adheres to the hand when these are put on and taken off, and droplets penetrate the protective clothing and the mask to cause infection from the mouth and the like.

In order to solve these problems, a virus-inactivating mask in which an antiviral agent is fixed to the surface of a mask (Patent Literature 1), a surgical mask that prevents the penetration of droplets (Patent Literature 2), and the like are developed.

CITATION LIST

Patent Literature

Patent Literature 1: WO2011/040035
Patent Literature 2: National Publication of International Patent Application No. 2014-503288

SUMMARY OF INVENTION

Technical Problem

However, the mask of Patent Literature 1 inactivates viruses adhering thereto but cannot prevent the penetration of materials containing a large amount of water, such as blood. In addition, for the mask of Patent Literature 2, the property of preventing the penetration of blood (hereinafter referred to as blood barrier properties) is excellent, but a fine filter is used correspondingly, and therefore it is difficult to breathe. Also, it is impossible to inactivate viruses, bacteria, and the like adhering thereto.

Accordingly, in order to solve the above problems, it is an object of the present invention to provide a mask that makes breathing easy and can prevent the penetration of blood, droplets, and the like.

Solution to Problem

Specifically, a first invention is a mask having an inner surface facing a wearer and an outer surface located opposite to the inner surface, comprising:

a first filter disposed on the outer surface and having air permeability and a water absorption capacity of 100% or more and less than 1000%;

a second filter layered on the first filter on the side of the inner surface and having air permeability and a water absorption capacity of less than 30%;

a third filter layered on the second filter on the side of the inner surface and formed of an electret filter having air permeability and a water absorption capacity of less than 50%; and a fourth filter disposed on the inner surface and having air permeability.

In addition, a second invention is a mask wherein in the first invention, a basis weight of the first filter is 15 g/m² or more and 40 g/m² or less.

Further, a third invention is a mask wherein in the first or second invention, the first filter and the second filter are each formed of a filter other than an electret filter.

Further, a fourth invention is a mask wherein in any of the first to third inventions, a water absorption capacity of the fourth filter is 100% or more and less than 1000%.

Further, a fifth invention is a mask wherein in the fourth invention, inorganic fine particles having bactericidal properties and/or antiviral properties are fixed to at least a portion of the first filter and/or the fourth filter.

Further, a sixth invention is a mask wherein in any of the first to fifth inventions, the first filter and the fourth filter are each formed of rayon fibers, and the second filter and the third filter are each formed of polypropylene fibers.

Advantageous Effects of Invention

According to the present invention, there is provided a mask that makes breathing easy and can prevent the penetration of blood, droplets, and the like. In addition, according to the above fifth invention, there is provided a mask that can inactivate bacteria and/or viruses contained in adhering blood and droplets.

DESCRIPTION OF EMBODIMENTS

An embodiment of the present invention is described below. As used herein, "water absorption capacity" means a value measured based on JIS L 1912: 1997. Specifically, water absorption capacity WA [%] is calculated based on the following (1) formula:

[Formula 1]

$$W_A = \frac{M_N - M_K}{M_K} \times 100 \quad (1)$$

wherein MK is the weight of a sample before immersion in water (the average value of five measured values), and MN is the weight of the sample after immersion in water (the average value of five measured values).

This embodiment is a mask which comprises four filters having air permeability and in which a first filter, a second filter, a third filter, and a fourth filter are layered in this order from the outermost layer (the layer farthest from a mask wearer) toward the inside. These filters are integrated by being layered along the thickness direction of the mask and welded. The integration treatment of these is not limited to welding and may be another method, for example, sewing.

First, the first filter forming the mask of the present invention will be described.

The first filter is characterized by having a water absorption capacity of 100% or more and less than 1000%, that is, comprising a material having hydrophilicity. The water absorption capacity of the first filter is preferably 100% or more and 900% or less, more preferably 100% or more and 850% or less. Most blood and droplets adhere to the first filter that is the outermost layer. At this time, the blood and droplets colliding the first filter are likely to spread along the surface of the first filter rather than moving to the second filter side because the first filter is hydrophilic. Therefore, the amounts of blood and droplets penetrating the first filter can be greatly decreased.

The material used for the first filter can be appropriately selected by those skilled in the art as long as it is a material having hydrophilicity likely to cause wetting and spreading. Natural fibers, regenerated fibers, semi-synthetic fibers, and the like are preferred. Examples of these fibers include cotton, kapok, hemp, wool, silk, Lyocell (registered trademark), Tencel (registered trademark), rayon, rayon PET blended fibers, viscose rayon, polynosic, cupra (registered trademark), casein fibers, regenerated silk, acetate, triacetate, oxidized acetate, and promix. Because of moderate strength and good texture, cotton, rayon, rayon PET blended fibers, and the like are particularly preferred.

In addition, the first filter has air permeability, and in order to also provide functions other than air permeability, as the material of the first filter, nonwoven fabrics are preferred. By using a nonwoven fabric, a particularly good feel and low irritativeness to the skin can be ensured, and the water absorbency can be improved due to the presence of the hydrophilic material of the first filter in three-dimensional directions (two-dimensional directions along the surface of the first filter, and the thickness direction of the first filter). The basis weight of the first filter is preferably 15 $g/m^2$ or more and 40 $g/m^2$ or less, more preferably 15 $g/m^2$ or more and 25/$m^2$ or less. When the basis weight is less than 15 $g/m^2$, blood and droplets are likely to pass through the first filter, and blood and droplets are less likely to be spread along the surface of the first filter as described above. In contrast, when the basis weight is greater than 40 $g/m^2$, the wearer feels suffocating. In addition, the amount of air flowing in from the gap between the mask and the wearer (face), other than inflow air from the outside surface of the mask (air passing through the first to fourth filters and flowing in), increases when the wearer draws his breath. That is, the amount of air inhaled without the mask increases, and the effect of mask wearing reduces, which is not preferred.

Further, inorganic fine particles having antibacterial and/or antiviral properties (hereinafter referred to as antibacterial-antiviral fine particles) are bonded to an outer surface of the first filter (at least one of the outside surface of the mask and the surface opposed to the second filter) via a binder.

The antibacterial-antiviral fine particles are fine particles of at least one inorganic compound selected from the group consisting of platinum(II) iodide, palladium(II) iodide, silver(I) iodide, copper(I) iodide, and copper(I) thiocyanate, exhibit antibacterial properties regardless of whether gram-positive or -negative, and can inactivate viruses regardless of the presence or absence of envelopes. In addition, the antibacterial-antiviral fine particles used in the present invention can inactivate bacteria and/or viruses even in the presence of proteins and lipids.

The virus inactivation mechanism of the antibacterial-antiviral fine particles is not necessarily clear at present, but it is considered that when the antibacterial-antiviral fine particles come into contact with water in air or in droplets, the oxidation-reduction reaction of some of them has some influence on electrical charges on the surface of viruses, membrane proteins, DNA, or the like adhering to the mask in this embodiment, to inactivate the viruses. Therefore, when the antibacterial-antiviral fine particles are present on a substrate having hydrophilicity (the outer surface of the filter), the antibacterial-antiviral fine particles are likely to act on bacteria and viruses because water in air or in droplets is likely to be retained on the substrate having hydrophilicity, which is preferred.

Here, the particle diameter of the antibacterial-antiviral fine particles is not particularly limited and can be appropriately set by those skilled in the art, but the average particle diameter is preferably 1 nm or more and less than 500 nm. When the average particle diameter is less than 1 nm, the antibacterial-antiviral fine particles are materially unstable, and therefore the antibacterial-antiviral fine particles aggregate by physical interaction, and it is difficult to uniformly fix the antibacterial-antiviral fine particles to the outer surface of the first filter. When the average particle diameter is 500 nm or more, the adhesiveness of the antibacterial-antiviral fine particles and the first filter decreases compared with less than 500 nm. As used herein, the average particle diameter refers to a volume average particle diameter.

In this embodiment, the antibacterial-antiviral fine particles are fixed to the first filter via a binder. The binder is not particularly limited, but silane monomers, and oligomers that are polymers of silane monomers, are preferred because they have low molecular weight and therefore are less likely to inhibit the contact of the antibacterial-antiviral fine particles with bacteria and viruses, and bacteria and viruses can be effectively inactivated. In addition, silane monomers, and oligomers that are polymers of silane monomers, also have high adhesiveness to the antibacterial-antiviral fine particles and the first filter, and therefore the antibacterial-antiviral fine particles can be stably fixed to the first filter.

In this manner, in the mask in this embodiment, when a silane monomer or an oligomer thereof is used as the binder, the exposed areas (the areas of the regions not covered with the binder) of the antibacterial-antiviral fine particles fixed to the first filter can be increased because the silane monomer or the oligomer thereof has sufficient fixing force even in a small amount. Thus, compared with a case where the antibacterial-antiviral fine particles are fixed to the first filter using a binder such as a synthetic resin other than a silane monomer or an oligomer thereof, the probability that bacteria and viruses adhering to the first filter surface come into contact with the antibacterial-antiviral fine particles can be increased. Therefore, the antibacterial-antiviral fine particles can efficiently inactivate bacteria and/or viruses even in a small amount.

Among the above silane monomers, silane coupling agents having unsaturated bond portions are preferably used. This is because coupling agents have a large number of hydrophilic groups (—OH groups) by hydrolysis, and therefore have the effect of keeping hydrophilicity high (keeping water absorption capacity) even if hydrophobic antibacterial-antiviral fine particles comprising inorganic fine particles are fixed to the first filter having high hydrophilicity.

In addition, the antibacterial-antiviral fine particles are firmly fixed to the first filter by a chemical bond to the silane monomer or the oligomer thereof, and therefore compared with a conventional case where a binder such as a synthetic resin other than a silane monomer or an oligomer thereof is used, the falling off of the antibacterial-antiviral fine particles from the first filter is greatly suppressed. Therefore, the mask in this embodiment can extend the time during which bacteria and/or virus inactivation action can be maintained, compared with conventional ones. By selecting a silane monomer, the antibacterial-antiviral fine particles may be retained on the first filter by a condensation reaction, an amide bond, a hydrogen bond, or an ionic bond, or van der Waals force, physical adsorption, or the like.

In this embodiment, the form in which the antibacterial-antiviral fine particles are retained on the first filter is not particularly limited and can be appropriately selected by those skilled in the art. For example, the antibacterial-antiviral fine particles may be scattered on the first filter. In addition, an assembly of the antibacterial-antiviral fine particles may be retained on the first filter in a planar or three-dimensional form. More specifically, the assembly can be retained in a form such as the form of dots, islands, or a thin film. In a case where the assembly is retained in a three-dimensional form, for the antibacterial-antiviral fine particles, those bonded to the first filter via the silane monomer or the oligomer thereof (referred to as antibacterial-antiviral fine particles a), and those bonded to the antibacterial-antiviral fine particles a via the silane monomer or the oligomer thereof are present.

Here, the amount of the antibacterial-antiviral fine particles retained on the mask in this embodiment can be appropriately set by those skilled in the art considering the purpose of use or application of the mask, and the particle diameter of the antibacterial-antiviral fine particles. Specifically, the amount of the antibacterial-antiviral fine particles is preferably 1.0% by mass to 80.0% by mass, more preferably 5.0% by mass to 60.0% by mass, based on the total of the substances (the binder and the antibacterial-antiviral fine particles) retained on the first filter. When the amount of the antibacterial-antiviral fine particles is less than 1.0% by mass, the activity of inactivating bacteria and/or viruses decreases compared with a case where the amount of the antibacterial-antiviral fine particles is 1.0% by mass or more. On the other hand, even if the amount of the antibacterial-antiviral fine particles is made larger than 80.0% by mass, there is no big difference in the effect of inactivating bacteria and/or viruses, compared with a case where the amount of the antibacterial-antiviral fine particles is within the range of 1.0% by mass to 80.0% by mass. In addition, when the amount of the antibacterial-antiviral fine particles is larger than 80.0% by mass, the binding properties of the oligomer formed by the condensation reaction of the silane monomer decrease due to the insufficient amount of the binder, and, compared with a case where the amount of the antibacterial-antiviral fine particles is 80.0% by mass or less, the antibacterial-antiviral fine particles are likely to detach from the first filter.

According to the mask in this embodiment, various viruses can be inactivated regardless of the type of genome, the presence or absence of an envelope, and the like. Examples of these viruses can include rhinoviruses, polioviruses, foot and mouth disease viruses, rotaviruses, noroviruses, enteroviruses, hepatoviruses, astroviruses, sapoviruses, hepatitis E viruses, influenza A, B, and C viruses, parainfluenza viruses, mumps viruses (epidemic parotitis), measles viruses, human metapneumoviruses, RS viruses, Nipah viruses, Hendra viruses, yellow fever viruses, dengue viruses, Japanese encephalitis viruses, West Nile viruses, hepatitis B and C viruses, eastern and western equine encephalomyelitis viruses, O'nyong-nyong viruses, rubella viruses, Lassa viruses, Junin viruses, Machupo viruses, Guanarito viruses, Sabia viruses, Crimean-Congo hemorrhagic fever viruses, sandfly fever, hantaviruses, Sin Nombre viruses, rabies viruses, Ebola viruses, Marburg viruses, bat lyssaviruses, human T-cell leukemia viruses, human immunodeficiency viruses, human coronaviruses, SARS coronaviruses, human parvoviruses, polyomaviruses, human papillomaviruses, adenoviruses, herpesviruses, varicella-zoster viruses, EB viruses, cytomegaloviruses, smallpox viruses, monkeypox viruses, cowpox viruses, molluscipox-viruses, parapoxviruses, and Zika viruses.

In addition, according to the mask in this embodiment, the bacteria that can be inactivated are not particularly limited either, and various bacteria and the like can be sterilized regardless of properties such as gram-positive and -negative properties, aerobic properties, and anaerobic properties. Examples of these bacteria can include *Escherichia coli*, *Staphylococcus aureus*, *Staphylococcus epidermidis*, streptococci, pneumococci, *Haemophilus influenzae*, *Bordetella pertussis*, *Salmonella enteritidis*, *Klebsiella pneumoniae*, *Pseudomonas aeruginosa*, vibrios, salmonellae, *Vibrio cholerae*, dysentery bacilli, *Bacillus anthracia*, *Mycobacterium tuberculosis*, *Clostridium botulinum*, *Clostridium tetani*, and streptococci.

Further, according to the mask in this embodiment, even if lipids and proteins are present in addition to bacteria and viruses as a result of the adhesion of, for example, droplets, the bacteria and/or viruses can be inactivated.

Therefore, according to the mask in this embodiment, bacteria and/or viruses adhering to the mask can be inactivated, and therefore the infection of the wearer can be prevented. Further, also when the mask after use is touched, secondary infection can be less likely to be caused.

Next, the second filter in this embodiment will be described.

The second filter in this embodiment is characterized by having a water absorption capacity of less than 30%. The water absorption capacity of the second filter is preferably less than 20%, more preferably less than 10%. The second filter has a water absorption capacity of less than 30% and therefore has a role in blocking droplets and blood penetrating the first filter, and assisting blood and droplets to move along the first filter. When the water absorption capacity is 30% or more, droplets and blood penetrate the second filter, which is not preferred.

The second filter is desirably a filter other than an electret filter. The electret filter has high dust collection efficiency and can capture fine particles and the like. However, when a filter having high dust collection efficiency is disposed at a position near the outer layer of a multilayer filter mask, like the second filter of the mask of this application, dust and the like are likely to cause clogging in a short time to cause a decrease in the function of the mask. Therefore, a filter having a higher dust collection effect is desirably disposed for an inside filter rather than an outside filter. As described later, in the mask in this embodiment, an electret filter is used for the third filter, and therefore particles and the like penetrating the second filter can be supplemented by the third filter. Thus, by using a filter other than an electret filter for the second filter, a mask less likely to cause clogging and having high dust collection efficiency can be obtained. In addition, when the second filter is formed of a filter other than an electret filter, the first filter is also preferably formed of a filter other than an electret filter. When both the first filter and the second filter are each formed of a filter other than an electret filter, clogging is even less likely to occur. Further, filters disposed on the outside surface or the inside surface of the mask are likely to come into contact with dust, and therefore when these filters are formed of electret filters, dust and the like are likely to cause clogging in a short time to cause a decrease in the function of the mask. Therefore, the first filter and the fourth filter are each preferably formed of a filter other than an electret filter. The electret filter is a charged body and therefore is formed of a hydrophobic material likely to be charged (that is, less likely to be formed of a hydrophilic material less likely to be charged). Therefore, a filter for which a hydrophilic material is used (for example, the first filter) is less likely to be formed as an electret filter.

As the material having a water absorption capacity of less than 30%, synthetic fibers are preferred. Specific examples of the material of the synthetic fibers include polyester, polypropylene, polyethylene terephthalate, nylon, acrylic, polyacrylic acid, polymethyl methacrylate, and the like. Polypropylene excellent in the property of preventing the penetration of blood is preferred.

The second filter in this embodiment also has air permeability like the above-described first filter, and in order to also provide functions other than air permeability, as the material of the second filter, nonwoven fabrics are preferred. By using a nonwoven fabric, a good feel and low irritativeness to the skin can be ensured, and the water repellency can be improved due to the presence of the material of the second filter having the above-described water absorption capacity, in three-dimensional directions (two-dimensional directions along the surface of the first filter, and the thickness direction of the first filter). The basis weight of the second filter is preferably 15 $g/m^2$ or more and 40 $g/m^2$ or less, more preferably 15 $g/m^2$ or more and 25/$m^2$ or less. When the basis weight is less than 15 $g/m^2$, blood and droplets are likely to pass through the second filter, and the second filter is less likely to play the above role of the second filter. In contrast, when the basis weight is greater than 40 $g/m^2$, the mask wearer feels suffocating.

Further, the third filter in this embodiment will be described.

The third filter in this embodiment is characterized by being formed of an electret filter having a water absorption capacity of less than 50%. The water absorption capacity of the third filter is preferably less than 40%, more preferably less than 30%.

An electret filter is known as a filter having high dust collection efficiency and therefore can efficiently collect viruses, bacteria, dust, and the like penetrating the first and second filters, even at low basis weight. When the third filter is not an electret filter, fine dust and the like may penetrate. In addition, when the electret filter is formed of a material having low water absorption capacity, like the second filter, droplets and blood penetrating the first and second filters can be finally blocked.

As the material having a water absorption capacity of less than 50%, synthetic fibers are preferred. Specific examples of the material of the synthetic fibers include polyester, polypropylene, polyethylene terephthalate, nylon, acrylic, polyacrylic acid, polymethyl methacrylate and the like. Polypropylene excellent in the property of preventing the penetration of blood is preferred.

The third filter in this embodiment also has air permeability like the above-described first and second filters, and in order to also provide functions other than air permeability, as the material of the third filter, nonwoven fabrics are preferred. By using a nonwoven fabric, a good feel and low irritativeness to the skin can be ensured, and the water repellency can be improved due to the presence of the material of the third filter having the above-described water absorption capacity, in three-dimensional directions (two-dimensional directions along the surface of the first filter, and the thickness direction of the first filter). The basis weight of the third filter is preferably 15 $g/m^2$ or more and 40 $g/m^2$ or less, more preferably 15 $g/m^2$ or more and 25/$m^2$ or less. When the basis weight is less than 15 $g/m^2$, blood and droplets are likely to pass through the third filter, and the third filter is less likely to play the above role of the third filter. In contrast, when the basis weight is greater than 40 $g/m^2$, the mask wearer feels suffocating.

Finally, the fourth filter in this embodiment will be described.

The fourth filter in this embodiment is characterized by having air permeability. The penetration of blood and droplets sometimes cannot be completely prevented by the first filter to the third filter, and therefore when the fourth filter is not provided, the blood barrier properties decrease. The fourth filter is not particularly limited as long as it has air permeability. But, the fourth filter is preferably hydrophilic because it directly touches the mask wearer, and therefore unless the water absorbency is high, water and the like contained in the breath remain inside the mask, and the mask wearer becomes uncomfortable. For example, the water absorption capacity of the fourth filter can be 100% or more and less than 1000%. Here, the water absorption capacity of the fourth filter is preferably 100% or more and 900% or less, more preferably 100% or more and 850% or less. Therefore, also for the material of the fourth filter, like the first filter, natural fibers, regenerated fibers, semi-synthetic fibers, and the like are preferred, and particularly cotton and rayon are preferred.

Further, antibacterial-antiviral fine particles may be fixed to an outer surface of the fourth filter (at least one of the surface exposed on the wearer side and the surface opposed to the third filter) by a binder, like the first filter. By fixing the antibacterial-antiviral fine particles to the outer surface of the fourth filter, bacteria and/or viruses contained in droplets and blood passing through the third filter by any chance can be inactivated. Moreover, even if the mask is used for a long period, the generation of an odor due to the multiplication of germs can be suppressed, and therefore a mask that has higher safety and can be used for a long period can be provided.

The average particle diameter and % by mass of the antibacterial-antiviral fine particles can be set like the antibacterial-antiviral fine particles fixed to the first filter. As the binder, a silane monomer or an oligomer thereof can be used.

Here, in the mask in this embodiment, it is preferred that the water absorption capacity of not only the first filter but the fourth filter is 100% or more and less than 1000%, and the antibacterial-antiviral fine particles are fixed to (retained on) at least a portion of these first filter and/or fourth filter. In the mask in this embodiment formed in this manner, the first filter and the fourth filter are likely to retain water, and therefore the antibacterial-antiviral fine particles retained on the filters are likely to come into contact with water, and the antibacterial properties and the antiviral properties are likely to improve. In addition, the first filter and the fourth filter are filters disposed on the outside surface or the inside surface of the mask and are disposed at positions where bacteria and/or viruses are likely to adhere. Therefore, more bacteria and viruses adhering to the mask are likely to be inactivated.

In addition, in the mask in this embodiment, it is preferred that the first filter and the fourth filter are each formed of rayon fibers, and the second filter and the third filter are each formed of polypropylene fibers.

The mask in this embodiment has been described in detail above, but the present invention is not limited to this and can also be in other modes. In this manner, when the mask of the present invention is used, the wearer can live comfortably, and at the same time the penetration of blood and droplets can also be prevented, and infection due to adhering bacteria and viruses can also be prevented.

EXAMPLES

Next, the present invention will be more specifically described by giving Examples. However, the present invention is not limited to only these Examples.

Example 1

A rayon PET blended nonwoven fabric (basis weight 20 g/m$^2$) was used as a first filter, a polypropylene nonwoven fabric (basis weight 20 g/m$^2$) was used as a second filter, a polypropylene electret filter 1 (MPER04 manufactured by Mitsui Chemicals, Inc., basis weight 20 g/m$^2$) was used as a third filter, and the same rayon PET blended nonwoven fabric (basis weight 20 g/m$^2$) as the first filter was used as a fourth filter. These four filters were welded in the order of the first, second, third, and fourth filters to provide the sample of Example 1.

Example 2

The sample of Example 2 was obtained by a method similar to that of Example 1 except that the first and fourth filters of Example 1 were changed to rayon nonwoven fabrics (basis weight 20 g/m$^2$).

Example 3

1.0% By mass of a commercial copper(I) iodide powder as an antibacterial-antiviral agent was added to ethanol, and further 1.4% by mass of zirconium oxide particles having methacryloxypropyltrimethoxysilane covalently bonded to their surfaces were added followed by pre-dispersion by a homogenizer for 5 minutes and then crushing and dispersion by a bead mill to obtain a slurry having an average particle diameter of 146 nm. The average particle diameter here refers to a volume average particle diameter. Next, 0.7% by mass of tetramethoxysilane was added to this slurry, and the same rayon nonwoven fabric as the first filter of Example 2 was spray-coated with the slurry and then dried at 120° C. for 3 minutes to obtain a first filter having antibacterial-antiviral properties used in Example 3. This first filter having antibacterial-antiviral properties, and the second, third, and fourth filters used in Example 2 were welded to provide the sample of Example 3.

Example 4

The sample of Example 4 was obtained by the same method as Example 3 except that the same material as the first filter of Example 3 was used as the fourth filter.

Example 5

The sample of Example 5 was obtained by the same method as Example 4 except that the basis weight of the rayon nonwoven fabric used for the first filter of Example 4 was changed to 15 g/m$^2$.

Example 6

The sample of Example 6 was obtained by the same method as Example 4 except that the basis weight of the rayon nonwoven fabric used for the first filter of Example 4 was changed to 40 g/m$^2$.

Example 7

The sample of Example 7 was obtained by the same method as Example 4 except that the second filter of Example 4 was changed to a polyethylene terephthalate (PET) nonwoven fabric (basis weight 20 g/m$^2$).

Example 8

The sample of Example 8 was obtained by the same method as Example 4 except that the third filter of Example 4 was changed to a PP electret filter 2 (EMO2010 manufactured by Toray Industries Inc, basis weight 20 g/m$^2$).

Example 9

The sample of Example 9 was obtained by the same method as Example 4 except that a cotton nonwoven fabric (basis weight 20 g/m$^2$) was used instead of the rayon nonwoven fabric used for the fourth filter of Example 4.

Comparative Example 1

The first, third, and fourth filters of Example 2 were weldered to obtain the sample of Comparative Example 1.

Comparative Example 2

The first, second, and fourth filters of Example 2 were weldered to obtain the sample of Comparative Example 2.

Comparative Example 3

The sample of Comparative Example 3 was obtained by the same method as Example 2 except that the same polypropylene nonwoven fabric (basis weight 20 g/m$^2$) as the second filter of Example 2 was used as the first filter.

Comparative Example 4

The sample of Comparative Example 4 was obtained by the same method as Example 2 except that the same rayon nonwoven fabric (basis weight 20 g/m$^2$) as the first filter of Example 2 was used as the second filter.

Comparative Example 5

The sample of Comparative Example 5 was obtained by the same method as Example 2 except that the same rayon nonwoven fabric (basis weight 20 g/m$^2$) as the first filter of Example 2 was used as the third filter.

Comparative Example 6

The first, second, and third filters of Example 2 were weldered to obtain the sample of Comparative Example 6.

The combinations of the above samples are shown in Table 1.

TABLE 1

| | First filter | | | Second filter | | Third filter | | Fourth filter | | |
|---|---|---|---|---|---|---|---|---|---|---|
| | Material | Antiviral agent | Basis weight (g/m2) | Material | Basist weight (g/m2) | Material | Basis weight (g/m2) | Material | Antiviral agent | Basis weight (g/m2) |
| Example 1 | Rayon PET blended | x | 20 | PP | 20 | PP electret 1 | 20 | Rayon PET blended | x | 20 |
| Example 2 | Rayon | x | 20 | PP | 20 | PP electret 1 | 20 | Rayon | x | 20 |
| Example 3 | Rayon | CuI | 20 | PP | 20 | PP electret 1 | 20 | Rayon | x | 20 |
| Example 4 | Rayon | CuI | 20 | PP | 20 | PP electret 1 | 20 | Rayon | CuI | 20 |
| Example 5 | Rayon | CuI | 15 | PP | 20 | PP electret 1 | 20 | Rayon | CuI | 20 |
| Example 6 | Rayon | CuI | 40 | PP | 20 | PP electret 1 | 20 | Rayon | CuI | 20 |
| Example 7 | Rayon | CuI | 20 | PET | 20 | PP electret 1 | 20 | Rayon | CuI | 20 |
| Example 8 | Rayon | CuI | 20 | PP | 20 | PP electret 2 | 20 | Rayon | CuI | 20 |
| Example 9 | Rayon | CuI | 20 | PP | 20 | PP electret 1 | 20 | Cotton | CuI | 20 |
| Comparative Example 1 | Rayon | x | 20 | None | | PP electret 1 | 20 | Rayon | x | 20 |
| Comparative Example 2 | Rayon | x | 20 | PP | 20 | None | | Rayon | x | 20 |
| Comparative Example 3 | PP | x | 20 | PP | 20 | PP electret 1 | 20 | Rayon | x | 20 |
| Comparative Example 4 | Rayon | x | 20 | Rayon | 20 | PP electret 1 | 20 | Rayon | x | 20 |
| Comparative Example 5 | Rayon | x | 20 | PP | 20 | Rayon | 20 | Rayon | x | 20 |
| Comparative Example 6 | Rayon | x | 20 | PP | 20 | PP electret 1 | 20 | None | | |

(Water Absorbency Test)

For water absorption capacity for the above samples (Examples 1 to 9 and Comparative Examples 1 to 6), a test was carried out based on Water absorbency test: Amount of water absorbed in JIS L 1912: 1997 "Test methods for nonwoven fabrics of medical use", and water absorption capacity (%) was calculated. The results are shown in Table 2.

(Blood Barrier Property Test)

A blood barrier property test for the above samples (Examples 1 to 9 and Comparative Examples 1 to 6) was performed based on ASTM F1862 "Standard Test Method for Resistance of Medical Face Masks to Penetration by Synthetic Blood". 32 Samples were provided, and a case where there was no blood penetration in 29 or more samples among the 32 samples was accepted. The artificial blood jet pressure at this time was performed at 160 mmHg. The results are shown in Table 2.

(Antiviral Property Evaluation)

0.4 g of each of the first filters and the fourth filters of Examples 2 to 9 and the first filter of Comparative Example 1 was sampled, each sample (0.4 g) was placed in a vial, and 0.2 ml of a virus liquid was dropped and allowed to act at 37° C. for 5 minutes. After the action for 5 minutes, 10 ml of an SCDLP culture medium was added, and the mixture was stirred using a Vortex mixer, to wash away the virus. Then, each reaction sample was diluted with an MEM diluent until it reached 10-2 to 10-5 (tenfold serial dilution). 100 μL of the sample liquid was inoculated into MDCK cells cultured in a petri dish. After standing for 90 minutes to adsorb the virus to the cells, a 0.7% agar culture medium was overlaid followed by culture in a 5% CO2 incubator at 34° C. for 48 hours and then formalin fixation and methylene blue staining. The number of plaques formed was counted to calculate virus infectivity titer (PFU: plaque-forming units). Here, for each of the first filter and the fourth filter in each sample, virus infectivity titer was calculated. The results are shown in Table 2.

TABLE 2

| | First filter | | Second filter | Third filter | Fourth filter | | |
|---|---|---|---|---|---|---|---|
| | Water absorption capacity (%) | Virus infectivity titer (PFU/0.1 ml, Log10) | Water absorption capacity (%) | Water absorption capacity (%) | Water absorption capacity (%) | Virus infectivity titer (PFU/0.1 ml, Log10) | Blood barrier properties |
| Example 1 | 140 | — | 9 | 24 | 140 | — | Accepted |
| Example 2 | 770 | 5.7 | 9 | 24 | 770 | 6.1 | Accepted |
| Example 3 | 702 | <1.3 | 9 | 24 | 770 | 5.8 | Accepted |
| Example 4 | 702 | <1.3 | 9 | 24 | 702 | <1.3 | Accepted |
| Example 5 | 683 | <1.3 | 9 | 24 | 702 | <1.3 | Accepted |
| Example 6 | 725 | <1.3 | 9 | 24 | 702 | <1.3 | Accepted |
| Example 7 | 702 | <1.3 | 15 | 24 | 702 | <1.3 | Accepted |
| Example 8 | 702 | <1.3 | 9 | 33 | 702 | <1.3 | Accepted |
| Example 9 | 702 | <1.3 | 9 | 24 | 754 | <1.3 | Accepted |
| Comparative Example 1 | 770 | 5.7 | | 24 | 770 | — | Rejected |
| Comparative Example 2 | 770 | — | 9 | | 770 | — | Rejected |
| Comparative Example 3 | 9 | — | 9 | 24 | 770 | — | Rejected |
| Comparative Example 4 | 770 | — | 770 | 24 | 770 | — | Rejected |
| Comparative Example 5 | 770 | — | 9 | 770 | 770 | — | Rejected |
| Comparative Example 6 | 770 | — | 9 | 24 | | — | Rejected |

In all Examples according to the present invention, the results of the determination of blood barrier properties were accepted. Compared with these results, in all of the samples of Comparative Examples 1, 2, and 6 in which the second, third, or fourth filter was absent, and the samples of Comparative Example 3 in which the water absorption capacity of the first filter was low, Comparative Example 4 in which the water absorption capacity of the second filter was high, and Comparative Example 5 in which the water absorption capacity of the third filter was high, the blood barrier properties were rejected. That is, it is indicated that the blood barrier properties decrease unless a nonwoven fabric substrate having high water absorption capacity (water absorption capacity 100% or more) is used for the first filter, and further hydrophobic nonwoven fabric substrates having low water absorption capacity (second filter: water absorption capacity 30% or less, third filter: water absorption capacity 50% or less) are used for the second and third filters, and the fourth filter is provided. Further, it was also confirmed that the samples of Examples 3 to 9 in which antiviral processing was performed had the high antiviral effect of the detection limit value or less in spite of the short time of 5 minutes. From the above results, the masks in the present Examples are excellent in blood barrier properties and also have a high antiviral effect and therefore can provide masks having blood barrier properties useful for secondary infection prevention.

The invention claimed is:

1. A mask having an inner surface configured to face a wearer and an outer surface located opposite to the inner surface, comprising:
    a first filter disposed on the outer surface and having air permeability and a water absorption capacity of 100% or more and less than 1000%;
    a second filter layered on the first filter on a side of the inner surface and having air permeability and a water absorption capacity of less than 30%;
    a third filter layered on the second filter on a side of the inner surface and formed of an electret filter having air permeability and a water absorption capacity of less than 50%; and
    a fourth filter disposed on the inner surface and having air permeability,
    wherein in the first filter is a outermost layer of the mask.

2. The mask according to claim 1, wherein the fourth filter has a water absorption capacity of 100% or more and less than 1000%.

3. The mask according to claim 2, wherein inorganic fine particles having bactericidal properties and/or antiviral properties are fixed to at least a portion of the first filter and/or the fourth filter.

4. The mask according to claim 1, wherein a basis weight of the first filter is 15 $g/m^2$ or more and less than or equal to 40 $g/m^2$.

5. The mask according to claim 1, wherein the first filter and the second filter are each formed of a filter other than an electret filter.

6. The mask according to claim 1, wherein
    the first filter and the fourth filter are each formed of rayon fibers, and
    the second filter and the third filter are each formed of polypropylene fibers.

* * * * *